United States Patent [19]

Houminer et al.

[11] Patent Number: 4,588,813
[45] Date of Patent: May 13, 1986

[54] 1-PYRAZINYL-1-PROPANONE DERIVATIVES USEFUL AS FLAVORANTS IN SMOKING COMPOSITIONS

[75] Inventors: Yoram Houminer; Everett W. Southwick; David L. Williams, all of Richmond, Va.

[73] Assignee: Philip Morris Incorporated, New York, N.Y.

[21] Appl. No.: 648,424

[22] Filed: Sep. 7, 1984

Related U.S. Application Data

[62] Division of Ser. No. 467,412, Feb. 17, 1983.

[51] Int. Cl.$^4$ .......................................... C07D 241/12
[52] U.S. Cl. .................................... 544/406; 426/537
[58] Field of Search ........................................ 544/406

[56] References Cited

U.S. PATENT DOCUMENTS

| | | | |
|---|---|---|---|
| 2,677,686 | 5/1954 | Smith et al. | 544/406 |
| 3,402,051 | 9/1968 | Roberts | 544/406 X |
| 3,767,428 | 10/1973 | Mookherjee et al. | 426/537 |
| 3,881,025 | 4/1975 | Flament | 544/406 X |
| 3,890,320 | 6/1975 | Wolt | 544/406 |
| 3,914,227 | 10/1975 | Pittet et al. | 544/406 |
| 3,917,872 | 11/1975 | Winter et al. | 426/537 |

FOREIGN PATENT DOCUMENTS 1244068 8/1971 United Kingdom .

OTHER PUBLICATIONS

Baggett et al., Journal of Chromatography, vol. 97, (1974), pp. 79–82.
Harllee et al., Tobacco International, Mar. 9, 1979, pp. 40–52; Mar. 23, 1979, pp. 18–42.
Schumacher et al., J. Agric. Food Chem., vol. 25, No. 2, 1977, pp. 310–319.

Primary Examiner—Donald G. Daus
Assistant Examiner—William A. Teoli, Jr.

[57] ABSTRACT

This invention provides smoking compositions which contain a monoacylpyrazine compound as a flavorant additive.

In one of its embodiments, this invention provides tobacco compositions which contain a monoacylpyrazine flavorant additive such as 1-pyrazinyl-2,2-dimethyl-1-propanone:

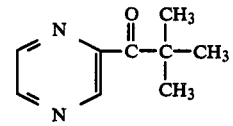

Under cigarette smoking conditions the above illustrated monoacylpyrazine additive flavors the mainstream smoke and enriches the aroma of the sidestream smoke.

4 Claims, No Drawings

1-PYRAZINYL-1-PROPANONE DERIVATIVES USEFUL AS FLAVORANTS IN SMOKING COMPOSITIONS

This application is a division of Ser. No. 467,412, filed Feb. 17, 1983.

BACKGROUND OF THE INVENTION

It has been established that alkylpyrazines are natural components of tobacco smoke, and that they most probably are important contributors to tobacco smoke flavor [A. Baggett et al, *J. Chromatog*, 97, 79 (1974)]. Further it has been disclosed in the patent literature that addition of alkylpyrazines to tobacco results in an improvement in the flavor of smoking compositions as perceived by a test panel.

British No. 1,244,068 describes a method for improving the smoke flavor of tobacco or a tobacco mixture which consists of treating the tobacco with a pyrazine derivative of the following chemical structure:

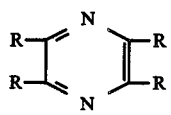

in which each R is independently a hydrogen atom, an aliphatic radical, an alicyclic radical or an aromatic hydrocarbon radical, such radicals having up to 9 carbon atoms, or R is a heterocyclic radical containing 4 to 9 carbon atoms.

Unlike alkylpyrazines which are ubiquitous in nature and heat-treated foodstuffs, acylpyrazines are more limited in their occurrence. For example, 2-acetyl-5-methylpyrazine and 2-acetyl-5-ethylpyrazine are reported as constituents of cocoa in Tobacco International, page 18ff (March 1979), and 1-(2-pyrazinyl)-1-butanone is tentatively identified as a water-soluble component of cigarette smoke in J. Agric. Food Chem., 25(2), 310 (1977).

Several acetylpyrazines are included in the F.E.M.A. listing of food additives as being useful for imparting a popcorn-nutty flavor to a foodstuff. The incorporation of acetylpyrazine, 2-acetyl-5-methylpyrazine or 2-acetyl-6-methylpyrazine as a popcorn-like flavorant in foodstuffs and tobacco is described in U.S. Pat. No. 3,402,051.

U.S. Pat. No. 3,767,428 disclosed a process for imparting a potato-like flavor to a foodstuff by the incorporation of 2-acetyl-3-ethylpyrazine.

U.S. Pat. No. 3,881,025 describes a process for enhancing the flavor of foodstuffs, beverages, tobacco products and the like which involves incorporating a combination of flavorant additives which include at least one pyrazine derivative of the formula:

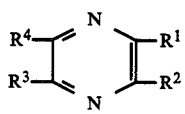

where the substituents $R^1$, $R^2$, $R^3$ and $R^4$ may be the same or different and either each represents a hydrogen atom or a saturated or unsaturated, cyclic or acyclic, linear or branched hydrocarbon radical, or $R^3$ together with $R^4$ may constitute a benzene ring, or one of them represents an acyl radical and each of the other a radical of the same type as those mentioned above.

U.S. Pat. No. 3,914,227 discloses the use of pyrazinyl alicyclic ketones as flavorants in foodstuffs and tobacco products. Pyrazinyl cyclohexyl ketone is described as a smoking composition additive which enhances the tobacco-like taste and aroma of a blended cigarette.

U.S. Pat. No. 3,917,872 describes the use of 2-formylpyrazine, 2-acetylpyrazine and 2-acetonylpyrazine as foodstuff and beverage flavorants.

There is continuing interest in the development of organic derivatives which can impart novel flavorant properties to smoking compositions, foodstuffs, beverages, and the like. A particular interest in pyrazines as flavorants or fragrances has stimulated the investigation of various types of substituted pyrazines which potentially have unique organoleptic properties.

Accordingly, it is an object of this invention to provide novel acylpyrazine compounds which exhibit a desirable combination of properties for application as flavorants.

It is a further object of this invention to provide smoking compositions containing a novel acylpyrazine flavorant additive, which smoking compositions are adapted to impart unique flavor and aroma to mainstream and sidestream smoke under smoking conditions.

Other objects and advantages of the present invention shall become apparent from the accompanying description and examples.

DESCRIPTION OF THE INVENTION

One or more objects of the present invention are accomplished by the provision of a smoking composition comprising an admixture of (1) combustible filler selected from natural tobacco, reconstituted tobacco and non-tobacco substitutes, and (2) between about 0.0001 and 2 weight percent, based on the total weight of filler, of a monoacylpyrazine flavorant selected from 1-pyrazinyl-2,2-dimethyl-1-propanone, 1-(2,3-dimethyl-5-pyrazinyl)-1-propanone, 1-(2,3,5-trimethyl-6-pyrazinyl)-1-propanone, 1-[5-(2-methyl-1-propyl)-2-pyrazinyl]-1-propanone and 1-[6-(2-methyl-1-propyl)-2-pyrazinyl]-1-propanone.

The monoacylpyrazine compounds listed above exhibit an unexpected combination of flavorant properties. In addition to being relatively stable and non-volatile under ambient storage conditions, the said monoacylpyrazine flavorants are characterized by subjective flavorant properties which are pleasant and sweet (e.g., like sweet chocolate) as compared to a closely related monoacetylpyrazine compound such as 2-acetyl-3-ethylpyrazine (e.g., with potato-like taste and aroma).

Each of the monoacylpyrazine compounds recited above represents a novel chemical structure not previously reported in the technical literature.

Preparation of Acylpyrazines

Various specific methods of synthesizing acylpyrazine derivatives are disclosed in U.S. patents such as U.S. Pat. Nos. 3,711,482; 3,767,428; 3,890,320; and 3,914,227; and the like.

In J. Chem., Soc., Perkin II, 2035 (1972) there is reported the acylation of protonated pyrazine derivatives. In a general procedure, a heteroaromatic compound (e.g., pyrazine) is acylated by reacting the compound with alkanal in the presence of t-butyl hydroperoxide and iron(II) sulfate in a homogeneous aqueous medium of acetic acid and sulfuric acid.

An efficient method for preparation of the present invention monoacylpyrazine compounds is that disclosed in patent application Ser. No. 307,262, now abandoned, incorporated herein by reference. The said process involves the steps of (1) providing a heterogeneous reaction medium consisting of a water-immiscible organic phase and an acidic aqueous phase, wherein the organic phase comprises a mixture of an aldehyde compound (RCHO) and a pyrazine compound corresponding to the formula:

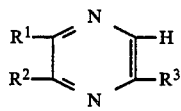

where $R^1$, $R^2$ and $R^3$ are substituents selected from hydrogen and alkyl groups, and $R^1$ and $R^2$ when taken together with connecting elements form an alicyclic or aromatic structure, and R in the aldehyde compound is a substituent selected from aliphatic, alicyclic and aromatic groups; (2) maintaining efficient contact between the organic and aqueous phases for a period of time sufficient to achieve acylation of the pyrazine compound in the presence of a free radical generating agent; and (3) recovering a monoacylpyrazine product corresponding to the formula:

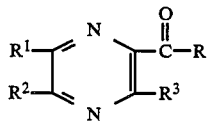

where R, $R^1$, $R^2$ and $R^3$ are substituents as previously defined.

The aldehyde (R—CHO) reactant can be any compound which does not contain any substituents which inhibit or prevent the free radical interaction of the aldehyde functionality with the pyrazine nucleus. It is preferred that the aldehyde reactant is at least partially soluble in the aqueous phase of the acylation system, in order to increase the rate and efficiency of the acylation reaction.

The pyrazine and aldehyde reactants can be employed over a wide range of molar ratios. It has been found convenient and advantageous to employ a molar ratio between about 0.5–10:1 of aldehyde to pyrazine in the acylation system.

The relative volumes of the respective immiscible phases in the acylation system are not critical, and typically the two phases will be approximately equal in volume.

The acidity of the aqueous phase is provided by the addition of a suitable acid reagent such as sulfuric acid, hydrochloric acid, phosphoric acid, and the like. The pH of the aqueous phase is below about 6, and preferably is in the range between about 1–5.

The acylation reaction between the pyrazine and aldehyde reactants is catalyzed by the inclusion of a free radical generating agent, in a quantity between about 1–50 weight percent, based on the weight of aldehyde reactant.

Illustrative of suitable free radical initiators are hydrogen peroxide; alkali metal or ammonium persulfates, perborates, peracetates and percarbonates; organic peroxides and hydroperoxides such as benzoyl peroxide, t-butylhydroperoxide and diisopropylperoxydicarbonate; and the like. The initiator may be associated with activating means (e.g., a redox system) which involves the use of compounds such as sulfites and thiosulfites, and redox reaction promoters such as transition metal ions (e.g., $Fe^{++}$).

Preparation Of Tobacco Compositions

The present invention smoking compositions can be prepared by admixing natural tobacco and/or reconstituted tobacco and/or a non-tobacco substitute with between about 0.0001 and 2 weight percent, based on the weight of the smoking composition, of a flavorant additive which corresponds to one of the invention monoacylpyrazine compounds set forth hereinabove.

An invention monoacylpyrazine flavorant additive can be incorporated into the tobacco in accordance with methods known and used in the art. Preferably the flavorant additive is dissolved in a solvent such as water, alcohol, or mixtures thereof, and then sprayed or injected into the tobacco or non-tobacco substitute matrix. Such method ensures an even distribution of the flavorant additive throughout the tobacco, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or non-tobacco substitute filler in a concentration between about 0.5–5 weight percent, based on the weight of filler, and then subsequently to blend the treated filler with filler which does not contain flavorant additive.

The term "non-tobacco substitute" is meant to include smoking filler materials such as are disclosed in U.S. Pat. Nos. 3,529,602; 3,703,177; 3,796,222; 4,019,521; 4,079,742; and references cited therein; incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

When a present invention monoacylpyrazine is incorporated into smoking material as a flavorant additive, and cigarettes are manufactured from the flavored blend, under smoking conditions the cigarettes have an increased flavor amplitude and/or sweetness and/or other desirable properties in comparison with control cigarettes which do not contain an invention monoacylpyrazine flavorant additive, as illustrated in Example VI.

The following examples are further illustrative of the present invention. The reactants and other specific ingredients are presented as being typical, and various modifications can be derived in view of the foregoing disclosure within the scope of the invention.

EXAMPLE I

This Example describes a general procedure for the preparation of monoacylpyrazines as illustrated by the preparation of 1-pyrazinyl-3-methyl-1-butanone.

To a stirring heterogeneous mixture of isovaleraldehyde (5.16 grams, 60 mmoles) and pyrazine (801 milligrams, 10 mmoles) in 5 milliliters of 3.4M sulfuric acid, at 3°–5° C., are added concurrently 70% t-butylhydroperoxide (5.4 grams, 42 mmoles) and a solution of ferrous sulfate (16.7 grams, 60 mmoles) in 40 milliliters of water over a 15 minute period. The resulting heterogeneous mixture is stirred an additional 1 hour, during which time the temperature is raised to 15° C. Solid sodium sulfite is then added until test with starch-iodide paper is negative.

The aqueous mixture is extracted with methylene chloride (3×100 milliliters), and the extracts are combined and washed with water. Optionally, the combined extract phase is washed with aqueous alkaline solution to remove acidic components. After drying (MgSO₄), the solvent is removed under reduced pressure to yield 2.5 grams of crude reaction mixture.

Analysis by gas chromatography indicates two major components in a 3:1 ratio, comprising the desired 1-pyrazinyl-3-methyl-1-butanone and isobutylpyrazine (identified by MS). Preparative thick layer chromatography (2000μ silica gel GF, developed with methylene chloride) provides a 12% yield of 1-pyrazinyl-3-methyl-1-butanone.

EXAMPLE II

Preparation Of 1-Pyrazinyl-2,2-Dimethyl-1-Propanone

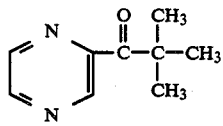

The reaction of pyrazine and trimethylacetaldehyde is conducted in the manner described in Example I on the same molar scale. Preparative thick layer chromatography (2000μ silica gel GF, developed with methylene chloride) of the crude reaction product provides an 11% yield of 1-pyrazinyl-2,2-dimethyl-1-propanone.

An analytically pure sample for odor and flavor evaluation is obtained by preparative GLC (¼″×15′ Carbowax® 20M-TPA). The structure is verified by IR, NMR and MS spectroscopy.

Anal. calc. for $C_9H_{12}N_2O$: C, 65.83; H, 7.37; N, 17.06; Found: C, 65.80; H, 7.50; N, 16.87.

EXAMPLE III

Preparation Of 1-(2,3-Dimethyl-5-Pyrazinyl)-1-Propanone

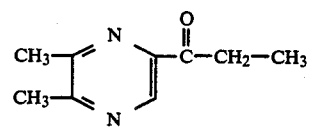

The reaction of 2,3-dimethylpyrazine and freshly distilled propionaldehyde is carried out as described in Example I on the same molar scale. Preparative thick layer chromatography (2000μ silica gel GF, developed in 5% acetone/hexane) of the crude reaction product gives a 25% yield of 1-(2,3-dimethyl-5-pyrazinyl)-1-propanone.

An analytically pure sample for odor and flavor evaluation is obtained by preparative GLC (¼″×15′ Carbowax® 20M-TPA). The structure is verified by spectroscopy.

Anal. calc. for $C_9H_{12}N_2O$: C, 65.83; H, 7.37; N, 17.06; Found: C, 65.75; H, 7.50; N, 17.20.

EXAMPLE IV

Preparation Of 1-(2,3,5-Trimethyl-6-pyrazinyl)-1-propanone

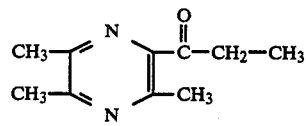

The reaction of trimethylpyrazine and freshly distilled propionaldehyde is carried out as described in Example I on the same molar scale. Preparative thick layer chromatography (2000μ silica gel GF, developed in 5% acetone/hexane) of the crude reaction product gives a 48% yield of 1-(2,3,5-trimethyl-6-pyrazinyl)-1-propanone (mp 65°–67° C.).

An analytically pure sample for odor and flavor evaluation is obtained by preparative GLC (¼″×15′ Carbowax® 20M-TPA). The structure is verified by spectroscopy.

Anal. calc. for $C_{10}H_{14}N_2O$: C, 67.39; H, 7.92; N, 15.72; Found: C, 67.24; H, 8.13; N, 15.62.

EXAMPLE V

Preparation Of
1-[3-(2-Methyl-1-propyl)-2-pyrazinyl]-1-propanone,
1-[5-(2-Methyl-1-propyl)-2-pyrazinyl]-1-propanone,
1-[6-(2-Methyl-1-propyl)-2-pyrazinyl]-1-propanone

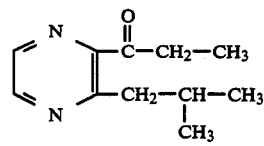

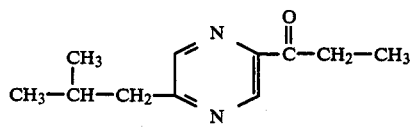

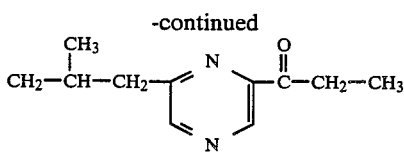

The reaction of isobutylpyrazine and freshly distilled propionaldehyde is carried out as described in Example I on the same molar scale. Preparative thick layer chromatography (2000μ silica gel GF, developed in 5% acetone/hexane) of the crude reaction product gives a 29% yield of a mixture of the three isomers.

Analytically pure samples of each isomer for odor and flavor evaluation are obtained by preparative GLC (¼″×15′ Carbowax® 20M-TPA). The 2,3-; 2,5-; and 2,6-isomer ratio is found to be 3:3:4 respectively. The structures are verified by IR, NMR and MS spectroscopy.

EXAMPLE VI

Preparation Of Smoking Compositions Containing An Invention Monoacylpyrazine

Cigarettes are fabricated employing a blend of tobaccos treated with an ethanolic solution of an invention monoacylpyrazine additive to provide 70–100 ppm of the compound by weight of the tobacco. The cigarettes are targeted to deliver 8 mg of tar per cigarette.

Untreated controls are prepared and the treated cigarettes are compared to the controls by an experienced smoking panel. The treated cigarettes are found to have the subjective test flavorant properties listed in the Table, as compared to the controls.

The subjective properties of the invention monoacylpyrazine flavorants generally are judged to be pleasant and sweet, as differing from the popcorn-like flavorant properties of 2-acetylpyrazine disclosed in U.S. Pat. No. 3,402,051, and the potato-like flavorant properties of 2-acetyl-3-ethylpyrazine disclosed in U.S. Pat. No. 3,767,428.

TABLE

| Ex. | Monoacylpyrazine | Subjective Flavorant Properties |
|---|---|---|
| II | [structure] | fruity, apple like |
| III | [structure] | sweet chocolate |
| IV | [structure] | fuller, more response, slightly chocolate |
| V | [structure] | sweet chocolate |
| V | [structure] | pleasant, woody, sweet |

What is claimed is:
1. 1-Pyrazinyl-2,2-dimethyl-1-propanone.
2. 1-(2,3-Dimethyl-5-pyrazinyl)-1-propanone.
3. 1-[5-(2-Methyl-1-propyl)-2-pyrazinyl]-1-propanone.
4. 1-[6-(2-Methyl-1-propyl)-2-pyrazinyl]-1-propanone.

* * * * *